United States Patent
Fjield et al.

(10) Patent No.: US 8,000,918 B2
(45) Date of Patent: Aug. 16, 2011

(54) MONITORING AND COMPENSATING FOR TEMPERATURE-RELATED ERROR IN AN ELECTROCHEMICAL SENSOR

(75) Inventors: Todd Fjield, Laguna Hills, CA (US); Michael J. Higgins, Huntington Beach, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

(21) Appl. No.: 12/205,634

(22) Filed: Sep. 5, 2008

(65) Prior Publication Data

US 2009/0030641 A1    Jan. 29, 2009

Related U.S. Application Data

(60) Provisional application No. 60/982,116, filed on Oct. 23, 2007.

(51) Int. Cl.
*G01D 18/00* (2006.01)
(52) U.S. Cl. ......................................................... 702/104
(58) Field of Classification Search .................... 702/23, 702/104
See application file for complete search history.

(56) References Cited

U.S. PATENT DOCUMENTS

| | | | |
|---|---|---|---|
| 4,223,110 A | 9/1980 | Phillips et al. |
| 4,271,278 A | 6/1981 | Phillips et al. |
| 4,352,360 A | 10/1982 | King |
| 4,398,346 A | 8/1983 | Underhill et al. |
| 4,430,397 A | 2/1984 | Untereker |
| 4,431,004 A | 2/1984 | Bessam |
| 4,465,743 A | 8/1984 | Skarstad et al. |
| 4,542,291 A | 9/1985 | Zimmerman |
| 4,549,952 A | 10/1985 | Columbus |
| 4,608,322 A | 8/1986 | Howard et al. |
| 4,703,756 A | 11/1987 | Gough |
| 4,937,444 A | 6/1990 | Zimmerman |
| 4,983,524 A | 1/1991 | Fujikawa et al. |
| 5,165,407 A | 11/1992 | Wilson et al. |
| 5,229,282 A | 7/1993 | Yoshioka et al. |
| 5,278,200 A | 1/1994 | Coury et al. |
| 5,331,966 A | 7/1994 | Bennett et al. |
| 5,352,348 A | 10/1994 | Young et al. |

(Continued)

FOREIGN PATENT DOCUMENTS

CN    1089651 A    7/1994

(Continued)

OTHER PUBLICATIONS

Wen-Yaw Chung, New ISFET interface circuit design with temperature compensation, Microelectronics Journal 37 (2006) 1105-1114, Jul. 17, 2006, p. 1105-1114).*

(Continued)

*Primary Examiner* — Tung S Lau
(74) *Attorney, Agent, or Firm* — Klarquist Sparkman, LLP (57) ABSTRACT

A method for compensating for a temperature-related error in an electrochemical sensor without using separate sources of temperature measurement by measuring sensor current, temporarily lowering sensor voltage to a first level below a reaction-sustaining threshold, measuring a first offset current, adjusting sensor voltage to a second level below the threshold, measuring a second offset current, calculating a difference between the offset currents, deriving a temperature compensation value from the difference based on empirical data, and adding the value to the measured sensor current. A computer system may execute the method as an algorithm stored in memory, provide automatic control of the sensor, and provide continuous display of corrected output values.

13 Claims, 7 Drawing Sheets

U.S. PATENT DOCUMENTS

| | | | |
|---|---|---|---|
| 5,390,671 A | 2/1995 | Lord et al. |
| 5,391,250 A | 2/1995 | Cheney, II et al. |
| 5,423,883 A | 6/1995 | Helland |
| 5,429,735 A | 7/1995 | Johnson et al. |
| 5,434,017 A | 7/1995 | Berkowitz et al. |
| 5,439,760 A | 8/1995 | Howard et al. |
| 5,455,123 A | 10/1995 | Helgeson et al. |
| 5,455,999 A | 10/1995 | Weiss et al. |
| 5,458,997 A | 10/1995 | Crespi et al. |
| 5,482,473 A | 1/1996 | Lord et al. |
| 5,486,215 A | 1/1996 | Kelm et al. |
| 5,497,772 A | 3/1996 | Schulman et al. |
| 5,538,511 A | 7/1996 | Van Antwerp |
| 5,549,985 A | 8/1996 | Heller et al. |
| 5,568,806 A | 10/1996 | Cheney, II et al. |
| 5,569,186 A | 10/1996 | Lord et al. |
| 5,586,553 A | 12/1996 | Halili et al. |
| 5,607,463 A | 3/1997 | Schwartz et al. |
| 5,607,565 A | 3/1997 | Azarnia et al. |
| 5,665,065 A | 9/1997 | Colman et al. |
| 5,695,623 A | 12/1997 | Michel et al. |
| 5,728,420 A | 3/1998 | Keogh |
| 5,741,211 A | 4/1998 | Renirie et al. |
| 5,766,839 A | 6/1998 | Johnson et al. |
| 5,777,060 A | 7/1998 | Van Antwerp |
| 5,779,364 A | 7/1998 | Cannelongo et al. |
| 5,779,665 A | 7/1998 | Mastrototaro et al. |
| 5,786,439 A | 7/1998 | Van Antwerp et al. |
| 5,788,678 A | 8/1998 | Van Antwerp |
| 5,838,546 A | 11/1998 | Miyoshi |
| 5,891,506 A | 4/1999 | Keogh |
| 5,914,179 A | 6/1999 | Inaba |
| 5,919,216 A | 7/1999 | Houben et al. |
| 5,925,552 A | 7/1999 | Keogh et al. |
| 5,945,319 A | 8/1999 | Keogh |
| 5,951,521 A | 9/1999 | Mastrototaro et al. |
| 5,965,380 A | 10/1999 | Heller et al. |
| 5,987,361 A | 11/1999 | Mortimer |
| 5,992,211 A | 11/1999 | Skrtic |
| 5,994,444 A | 11/1999 | Trescony et al. |
| 5,997,927 A | 12/1999 | Gics |
| 6,017,741 A | 1/2000 | Keogh |
| 6,033,719 A | 3/2000 | Keogh |
| 6,038,475 A | 3/2000 | Sikorski et al. |
| 6,071,391 A | 6/2000 | Gotoh et al. |
| 6,093,167 A | 7/2000 | Houben et al. |
| 6,093,172 A | 7/2000 | Funderburk et al. |
| 6,093,506 A | 7/2000 | Crespi et al. |
| 6,101,973 A | 8/2000 | Stewart et al. |
| 6,118,652 A | 9/2000 | Casby et al. |
| 6,125,291 A | 9/2000 | Miesel et al. |
| 6,129,742 A | 10/2000 | Wu et al. |
| 6,134,459 A | 10/2000 | Roberts et al. |
| 6,134,461 A | 10/2000 | Say et al. |
| 6,135,978 A | 10/2000 | Houben et al. |
| D433,755 S | 11/2000 | Mastrototaro et al. |
| 6,143,354 A | 11/2000 | Koulik et al. |
| 6,144,866 A | 11/2000 | Miesel et al. |
| 6,163,723 A | 12/2000 | Roberts et al. |
| 6,175,752 B1 | 1/2001 | Say et al. |
| 6,176,988 B1 | 1/2001 | Kessler |
| 6,198,952 B1 | 3/2001 | Miesel |
| 6,200,265 B1 | 3/2001 | Walsh et al. |
| 6,205,358 B1 | 3/2001 | Haeg et al. |
| 6,212,416 B1 | 4/2001 | Ward et al. |
| 6,218,016 B1 | 4/2001 | Tedeschi et al. |
| 6,223,083 B1 | 4/2001 | Rosar |
| 6,248,067 B1 | 6/2001 | Causey, III et al. |
| 6,252,032 B1 | 6/2001 | Van Antwerp et al. |
| 6,254,586 B1 | 7/2001 | Mann et al. |
| 6,261,280 B1 | 7/2001 | Houben et al. |
| 6,274,265 B1 | 8/2001 | Kraska et al. |
| 6,284,478 B1 | 9/2001 | Heller et al. |
| 6,293,925 B1 | 9/2001 | Safabash et al. |
| 6,295,473 B1 | 9/2001 | Rosar |
| 6,303,179 B1 | 10/2001 | Koulik et al. |
| D452,323 S | 12/2001 | Mastrototaro et al. |
| 6,329,161 B1 | 12/2001 | Heller et al. |
| 6,340,421 B1 | 1/2002 | Vachon et al. |
| 6,360,888 B1 | 3/2002 | McIvor et al. |
| 6,368,274 B1 | 4/2002 | Van Antwerp et al. |
| 6,413,393 B1 | 7/2002 | Van Antwerp et al. |
| 6,418,332 B1 | 7/2002 | Mastrototaro et al. |
| 6,424,847 B1 | 7/2002 | Mastrototaro et al. |
| 6,438,407 B1 | 8/2002 | Ousdigian et al. |
| 6,456,875 B1 | 9/2002 | Wilkinson et al. |
| 6,462,162 B2 | 10/2002 | Van Antwerp et al. |
| 6,477,395 B2 | 11/2002 | Schulman et al. |
| 6,484,045 B1 | 11/2002 | Holker et al. |
| 6,484,046 B1 | 11/2002 | Say et al. |
| D469,540 S | 1/2003 | Holker et al. |
| 6,512,939 B1 | 1/2003 | Colvin et al. |
| 6,520,326 B2 | 2/2003 | McIvor et al. |
| 6,558,345 B1 | 5/2003 | Houben et al. |
| 6,558,351 B1 | 5/2003 | Steil et al. |
| 6,558,734 B2 | 5/2003 | Koulik et al. |
| 6,560,471 B1 | 5/2003 | Heller et al. |
| 6,565,509 B1 | 5/2003 | Say et al. |
| 6,572,542 B1 | 6/2003 | Houben et al. |
| 6,572,748 B1 | 6/2003 | Herrmann |
| 6,577,899 B2 | 6/2003 | Lebel et al. |
| 6,592,746 B1 | 7/2003 | Schmid-Schoenbein et al. |
| 6,605,039 B2 | 8/2003 | Houben et al. |
| 6,617,142 B2 | 9/2003 | Keogh et al. |
| 6,641,533 B2 | 11/2003 | Causey, III et al. |
| 6,642,015 B2 | 11/2003 | Vachon et al. |
| 6,666,821 B2 | 12/2003 | Keimel |
| 6,669,663 B1 | 12/2003 | Thompson |
| 6,671,554 B2 | 12/2003 | Gibson et al. |
| 6,731,976 B2 | 5/2004 | Penn et al. |
| 6,784,274 B2 | 8/2004 | Van Antwerp et al. |
| 6,809,507 B2 | 10/2004 | Morgan et al. |
| 6,809,653 B1 | 10/2004 | Mann et al. |
| 6,811,659 B2 | 11/2004 | Vachon et al. |
| 6,840,904 B2 | 1/2005 | Goldberg |
| 6,879,861 B2 | 4/2005 | Benz et al. |
| 6,892,085 B2 | 5/2005 | McIvor et al. |
| 6,895,263 B2 | 5/2005 | Shin et al. |
| 6,895,265 B2 | 5/2005 | Silver |
| 6,899,813 B2 | 5/2005 | Dolecek et al. |
| 6,908,535 B2 | 6/2005 | Rankin et al. |
| 6,915,147 B2 | 7/2005 | Lebel et al. |
| 6,922,330 B2 | 7/2005 | Nielsen et al. |
| 6,923,936 B2 | 8/2005 | Swanson et al. |
| 6,940,141 B2 | 9/2005 | Kinsman |
| 6,942,518 B2 | 9/2005 | Liamos et al. |
| 6,959,247 B2 * | 10/2005 | Neel et al. ........................ 702/19 |
| 6,960,466 B2 | 11/2005 | Pamidi et al. |
| 6,972,423 B2 | 12/2005 | Welland et al. |
| 6,973,706 B2 | 12/2005 | Say et al. |
| 6,985,764 B2 | 1/2006 | Mason et al. |
| 6,991,096 B2 | 1/2006 | Gottlieb et al. |
| 7,003,336 B2 | 2/2006 | Holker et al. |
| 7,003,340 B2 | 2/2006 | Say et al. |
| 7,003,341 B2 | 2/2006 | Say et al. |
| 7,006,858 B2 | 2/2006 | Silver et al. |
| 7,018,336 B2 | 3/2006 | Enegren et al. |
| 7,022,072 B2 | 4/2006 | Fox et al. |
| 7,029,444 B2 | 4/2006 | Shin et al. |
| 7,083,712 B2 | 8/2006 | Morita et al. |
| 7,122,390 B2 | 10/2006 | Kinsman |
| 7,279,174 B2 | 10/2007 | Pacetti et al. |
| 2003/0178998 A1 * | 9/2003 | Ikura et al. ........................ 324/448 |
| 2004/0050694 A1 | 3/2004 | Yang et al. |
| 2004/0183213 A1 | 9/2004 | Hsu |
| 2004/0191428 A1 | 9/2004 | Tsuda et al. |
| 2005/0000829 A1 | 1/2005 | Morita et al. |
| 2005/0027463 A1 * | 2/2005 | Goode et al. ...................... 702/22 |
| 2005/0069925 A1 | 3/2005 | Ford et al. |
| 2005/0177035 A1 | 8/2005 | Botvinick |
| 2005/0233407 A1 | 10/2005 | Pamidi et al. |
| 2006/0108236 A1 | 5/2006 | Kasielke et al. |
| 2006/0127964 A1 | 6/2006 | Ford et al. |
| 2006/0282001 A1 | 12/2006 | Noel et al. |
| 2006/0287591 A1 * | 12/2006 | Ocvirk et al. ..................... 600/347 |
| 2007/0200254 A1 | 8/2007 | Curry |
| 2007/0202562 A1 | 8/2007 | Curry |

| | | | |
|---|---|---|---|
| 2007/0202672 | A1 | 8/2007 | Curry |
| 2007/0219441 | A1 | 9/2007 | Carlin et al. |
| 2008/0029390 | A1 | 2/2008 | Roche et al. |
| 2008/0033264 | A1 | 2/2008 | Lonneker-Lammers |
| 2008/0125751 | A1 | 5/2008 | Fjield et al. |
| 2008/0200788 | A1 | 8/2008 | Brister et al. |
| 2009/0023222 | A1* | 1/2009 | Wu et al. .................. 436/95 |

FOREIGN PATENT DOCUMENTS

| | | |
|---|---|---|
| DE | 3940113 A1 | 7/1990 |
| DE | 10 2004 056587 | 5/2006 |
| DE | 20 2006 016617 | 2/2007 |
| EP | 0 351 851 | 1/1990 |
| EP | 1 889 568 A1 | 2/2008 |
| EP | 2 040 065 A1 | 3/2009 |
| FR | 2331017 A1 | 6/1977 |
| FR | 2359421 A2 | 2/1978 |
| FR | 2606151 A1 | 5/1988 |
| JP | 56-155850 | 12/1981 |
| JP | 58-113744 | 7/1983 |
| JP | 62-000848 | 1/1987 |
| JP | 62-214341 | 9/1987 |
| JP | 63-005254 | 1/1988 |
| JP | 63-061157 | 3/1988 |
| JP | 05-099754 A | 4/1993 |
| JP | 06-094671 | 4/1994 |
| JP | 08-262026 | 10/1996 |
| JP | 09-184819 A | 7/1997 |
| JP | 09-250998 A | 9/1997 |
| JP | 09-297832 A | 11/1997 |
| WO | 96/11626 A | 4/1996 |
| WO | 97/29847 | 8/1997 |
| WO | 98/38112 | 9/1998 |
| WO | 99/30152 | 6/1999 |
| WO | 02/102224 | 12/2002 |
| WO | 2004/090533 A1 | 10/2004 |
| WO | 2004/113912 | 12/2004 |
| WO | 2005/018443 A1 | 3/2005 |
| WO | 2005/074612 | 8/2005 |
| WO | 2006/05033 A2 | 1/2006 |
| WO | 2007/098187 | 8/2007 |
| WO | 2007/100588 | 9/2007 |

OTHER PUBLICATIONS

Lisette B. Verbrugge MD, Deborah Crisis, RN, M Higgins BSce, MBA and Harry B van Wezel MD, PhD, "Accuracy of a Prototype Central Venous Continuous Amperometric Glucose Sensor," American Society of Anesthesiology (ASA) meeting in Oct. 2007.

Berger, et al., Structure and Interactions in Covalently and Ionically Crosslinked Chitosan Hydrogels for Biomedical Applications, Europ. J. Pharm. Biopharm., vol. 57, No, 1, pp. 19-34 (2004).

Fiorito et al..; Glucose Amperometric Biosensor Based on the Co-immobilizationi of Glucose Oxidase (GOx) and Ferrocene in Poly(pyrrole) Generated from ethanol/ water mixtures; J. Braz. Chem. Soc., vol. 12, No. 6 729-733, 2001.

Garg et al., "Improvement in Glycemic Excursions with a Transcutaneous, Real-Time Continuous Glucose Sensor, " Diabetes Care, (2006) 29: 44-50.

Krajewska; "Application of chitin- and chitosan based materials for enzyme immobilization: a review;" Enzyme Microb Technol 35 (2004), pp. 126-139.

Markey et al., "Immobilization of Catalase and Glucose Oxidase on Inorganic Supports," Biotechnology and Engineering (1975) 17:285.

Miao, et al..; "Amperometric Glucose Biosensor Based on Immobilization of Glucose Oxidase in Chitosan Matrix cross-linked with glutaraldehyde," Electroanalysis (2001) 46:347-49.

Renard, "Implantable Glucose Sensors for Diabetes Monitoring, " Minim Invasive Ther Allied Technol, 13:78-86 (2004).

Sternberg, et al., "Study and Development of Multilayer Needle-type Enzyme-based Glucose Microsensors," Biosensors 4: 27-40 (1988).

Urban, et al.; "Minitaurized thin-film biosensors using covalently immobilized glucose oxidase," May 4, 1990; accepted Jan. 23, 1991; Biosensors & Bioelectronics 6 (1991) 555-562.

Updike et al., "The Enzyme Electrode," Nature. vol. 214: 986 (1967).

Wang, "Glucose Biosensors: 40 Years of Advances and Challenges," Electroanalysis, vol. 13, No. 12, pp. 983-988 (2001).

European Patent Office as the International Searching Authority, International Search Report, Nov. 27, 2008, Europe (EP).

International Search Report for PCT/US2008/078535, dated Feb. 6, 2009.

Luis P. Leon, Musa Sansur, Lloyd R. Snyder, and Csaba Horvath, "Continuous-Flow Analysis for Glucose, Triglycerides, and ATP with Immobilized Enzymes in Tubular Form," Clinical Chemistry, vol. 23, No. 9, 1977, pp. 1556-1562.

* cited by examiner

MONITORING AND COMPENSATING FOR TEMPERATURE-RELATED ERROR IN AN ELECTROCHEMICAL SENSOR

CROSS-REFERENCE TO RELATED APPLICATIONS

This application claims priority from U.S. Provisional Patent Application No. 60/982,116, filed Oct. 23, 2007, which is also hereby incorporated herein by reference.

BACKGROUND

1. Field of the Invention

The invention relates generally to temperature compensation in electrochemical sensors. More specifically, the invention relates to automated compensation for temperature-related error in an intravenous amperometric sensor.

2. Description of Related Art

There are many applications for electrochemical sensors. One class of electrochemical sensors, known as amperometric biosensors, has many potential applications in the health care industry. For example, recent advances in the art of glucose monitoring are considering systems that continuously monitor blood glucose levels using an intravenous amperometric glucose sensor installed in a large blood vessel. The intravenous sensor continually outputs an electrical signal representing blood glucose level to a computer system that displays the level in real time for the attending physician. This allows the physician to take corrective action in case the blood glucose level becomes too high or too low. In an ICU or other emergency situation, the ability to immediately monitor and control blood glucose levels, particularly for diabetic patients, can mean the difference between life and death.

The accuracy of the output of the biosensor is therefore very important. Among many variables that can affect sensor accuracy is temperature. An amperometric sensor is typically calibrated at normal body temperature. When the sensor is immersed in the patient's bloodstream, it produces an electrical current in response to chemical reactions that occur on the surface of the sensor. Changes in body temperature are likely to affect the reaction rate, causing a loss of accuracy as the sensor outputs more or less current than it would at normal body temperature. The infusion of fluids through a catheter in the immediate vicinity of the sensor can also cause temperature-related errors if the infused fluids have a temperature different than the body temperature. The sensors can also be affected by exposure to room temperatures prior to insertion into the body. Depending on the location of the biosensor and the configuration of the device in which the biosensor is located, temperature changes may cause the current produced by the biosensor to change for the same glucose concentration, thereby invalidating the calibration curves. This may cause the accuracy of these biosensors to be unacceptable for clinical use and perhaps unreliable for guiding therapy.

A prior solution addressing the temperature-dependency problem of amperometric sensors includes withdrawing a sample of blood and measuring the glucose level in an isolated static environment with constant temperature. This solution, however, is not practical for use in an ICU, where time is of the essence. Another solution involves withdrawing a sample of blood across a biosensor and recirculating the blood back to the patient. This solution adds considerably to the complexity of the monitoring system and is difficult to implement in practice, due to the limited number of patient access sites, which are usually reserved for transfusions of blood and medicines. These solutions do not compensate for the temperature changes but rather seek to avoid the possibility of temperature changes.

Another solution involves using a separate temperature sensing element, such as a thermistor or a silver trace or other device, having a resistance that changes with temperature. However, the separate sensing element adds complexity to the monitoring system, takes up additional space within the catheter, and adds to the risk of infection, among other disadvantages.

With an increasing trend toward using amperometric sensors in health care and other industries, and especially in view of ongoing demand for improvements in glucose monitoring, a need exists for a more practical solution for temperature compensation in biosensor electrodes to provide reliable measurements despite a change in surrounding temperature.

SUMMARY

A system and method for compensating for temperature-related errors in an electrochemical sensor is provided. The system and method has industrial and medical applications, particularly in instrumentation systems employing amperometric sensors that are calibrated at a reference temperature and are therefore susceptible to temperature-related errors. These amperometric sensors output an electrical current proportional to an analyte concentration or to another parameter of interest when an excitation voltage is applied to the sensor at a level above a reaction-sustaining threshold such as an oxidation or reduction threshold. The system and method are described primarily in the context of an intravenous amperometric glucose sensor for use in emergency medical procedures.

A method may include measuring current output from the sensor, temporarily lowering sensor voltage to a first voltage level below the reaction-sustaining threshold, measuring an offset current corresponding to the first voltage level, adjusting sensor voltage to a second voltage level below the reaction-sustaining threshold, measuring an offset current corresponding to the second voltage level, calculating a difference between the offset currents, deriving a temperature compensation value based in part on the difference, and adding the temperature compensation value to the measured current output to obtain an output value corrected for temperature. Deriving the temperature compensation value may include using a computer system to retrieve a value from a lookup table stored in memory, or it may involve using a computer system to execute an algorithm that calculates a value according to a formula based on empirical data.

A system may compensate for temperature-related errors in an amperometric sensor that outputs a signal current proportional to an analyte concentration of interest, such as blood glucose concentration, when a voltage is applied to the sensor. The system may include a sensor having a working electrode, a potentiostat circuit for adjusting voltage applied to the working electrode, a processor coupled to a memory, and temperature compensation software stored in the memory and executable by the processor. In response to the processor executing the software, the potentiostat circuit temporarily lowers the voltage of the working electrode below a reaction-sustaining threshold to obtain a temperature compensation value for correcting sensor output when the voltage of the working electrode is raised above the reaction-sustaining threshold. The system may include a sensor control unit as an interface between the potentiostat analog circuit and the processor digital circuit, and a display unit for continuous display of corrected analyte concentration.

DETAILED DESCRIPTION

The invention discloses technology that compensates for temperature-related errors in the output of electrochemical sensors. The invention uses the response of the sensor itself to detect temperature, without the need for separate temperature measuring devices. This advancement has particular importance in sensing applications with spatial restrictions, such as certain invasive medical procedures. For example, an amperometric sensor may be used to monitor blood chemistry or other medical conditions in a patient. The sensor may be mounted on a catheter and inserted into the patient intravenously to allow for continuous monitoring of an analyte of interest. During installation, the catheter is carefully maneuvered through a blood vessel until it reaches a desired internal location. In a procedure such as this, there is little to no additional space available on the catheter for accommodating ancillary devices such as temperature sensors.

One application of the invention is in a continuous analyte monitoring system employing an amperometric sensor. Amperometric sensors (e.g., enzyme electrodes) generate electrical current produced by a chemical reaction of some medium that comes into contact with a substance such as an enzyme that is located on the surface of the sensor. Typically, the sensor is energized with an excitation voltage at a threshold level sufficient to sustain a chemical reaction. Based on the sensor type, the amount of electrical current generated by the sensor may determine a chemical concentration in the medium. In one embodiment, the monitoring system may be a glucose monitoring system and the amperometric sensor may be a glucose sensor. The glucose sensor may include an enzyme electrode partially coated with the enzyme glucose oxidase.

When installed inside a patient intravenously via a catheter, the glucose sensor may continually output an electrical signal indicative of blood glucose level. The signal may be fed to a computerized monitoring system that continuously or intermittently displays this information to an attending physician or other health care provider. The monitoring system automatically detects temperature by lowering the excitation voltage below the reaction-sustaining threshold temporarily, to obtain readings from which temperature may be derived. The monitoring system determines a correction factor to compensate for a temperature-related error in the output of the sensor. The monitoring system may raise sensor voltage back to a reaction-sustaining level and may apply the correction factor to subsequent readings.

Figure 1A:
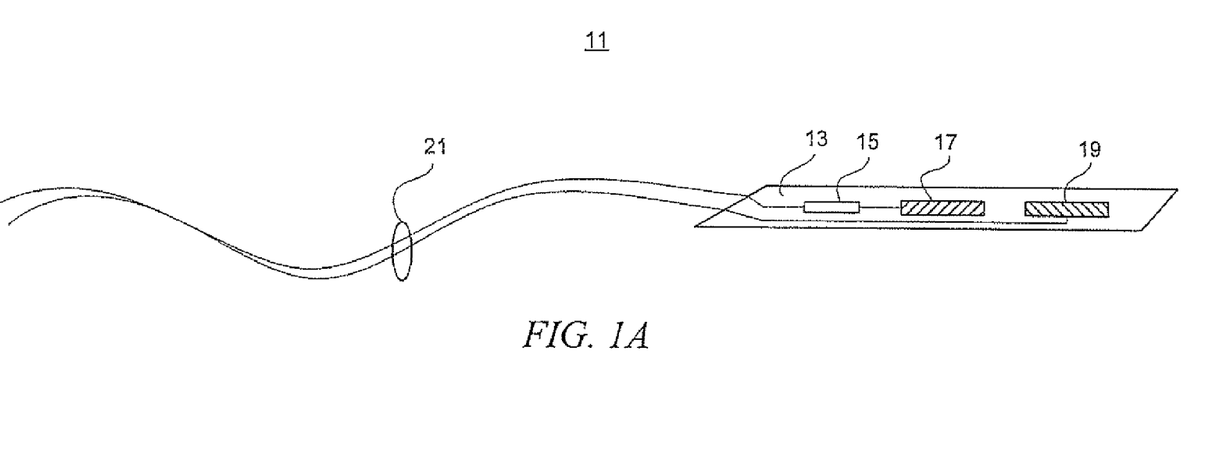
FIGS. 1A and 1B are top views of intravenous electrochemical sensors disposed on flex circuits for sensing an analyte and outputting a signal that is correctable for temperature.
Figure 1B:
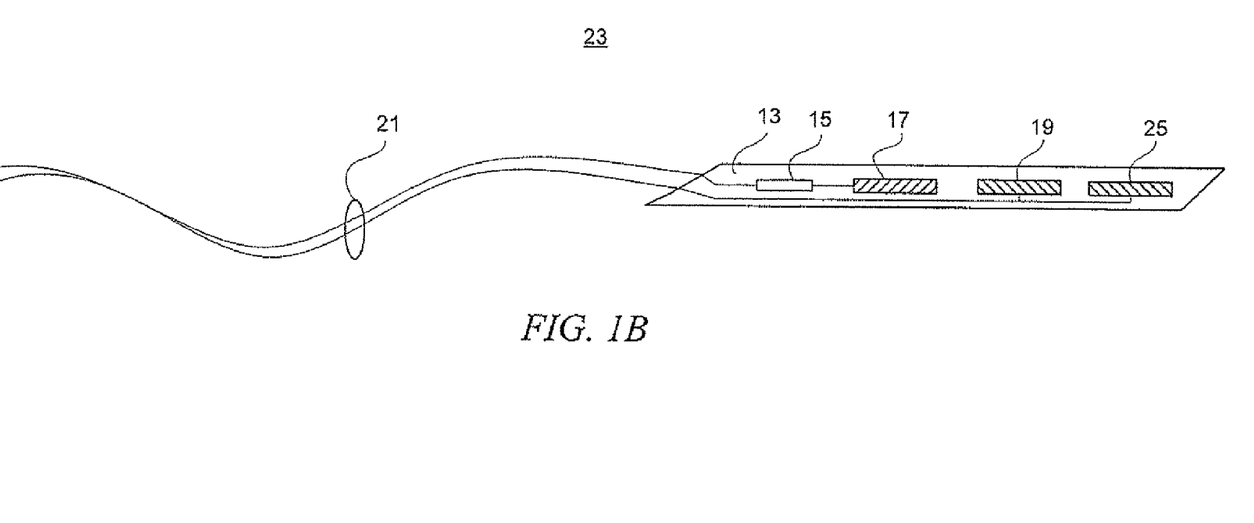

FIGS. 1A and 1B are top views of intravenous electrochemical sensors 11 and 23 disposed on a substrate 13 (e.g., a flex circuit) for sensing an analyte and outputting a signal that is correctable for temperature. Sensor 11 may be manufactured using flex circuit technology to miniaturize the sensor 11 for intravenous installation via a catheter. Sensor 11 may include a substrate 13, a reference electrode 15, a counter electrode 17, and a working electrode 19. There may be more electrodes on sensor 11 depending on the application. Electrical wires 21 provide power to the electrodes for sustaining an oxidation or reduction reaction, and may also carry signal currents to a detection circuit in the sensing system.

A sensing system derives, from the signal currents, a value indicative of a parameter being measured by sensor 11. The parameter being measured may be an analyte of interest that occurs in the medium to which sensor 11 is exposed. For example, if sensor 11 is a glucose sensor immersed within the bloodstream of a patient, the analyte of interest may be hydrogen peroxide, formed from reaction of the glucose in the blood with glucose oxidase on the sensor. In this embodiment, the amount of signal current produced by sensor 11 is proportional to the concentration of hydrogen peroxide, and thus also proportional to the concentration of blood glucose.

The sensing system may include a potentiostat that regulates an energization voltage applied to each of the electrodes 17 and 19. The energization voltages may change in response to control signals from a signal processor in the sensing system. The potentiostat keeps the electric potential of working electrode 19 (or counter electrode 17) constant in relation to reference electrode 15 by detecting resistance, and varying current accordingly, so that the desired potential is maintained. Control of electrode potential may be affected by simple application of Ohm's Law. In the same way, the potentiostat can raise or lower the potential of working electrode 19 (or counter electrode 17) by raising or lowering current according to the resistance detected or according to commands from the processor.

Sensor 11 may work on an amperometric measurement principle where working electrode 19 is held at a positive potential relative to counter electrode 17 to sustain a chemical reaction. For a glucose sensor bearing a glucose oxidase enzyme, the positive potential may be raised to a level sufficient to sustain an oxidation reaction of hydrogen peroxide, which is the result of a reaction of glucose with the glucose oxidase. Thus, working electrode 19 functions as an anode and collects electrons produced on its surface that result from the oxidation reaction. These electrons flow into working electrode 19 as an electrical current. With working electrode 19 coated with glucose oxidase, the oxidation of glucose produces a hydrogen peroxide molecule for every molecule of glucose, when working electrode 19 is held at a positive potential between about +450 mV and about +650 mV. The hydrogen peroxide produced oxidizes at the surface of working electrode 19 according to the equation:

$$H_2O_2 \rightarrow 2H^+ + O_2 + 2e^- \qquad (1)$$

The equation indicates that two electrons are produced for every hydrogen peroxide molecule oxidized. Thus, under certain conditions, the amount of electrical current is proportional to the hydrogen peroxide concentration. Since one hydrogen peroxide molecule is produced for every glucose molecule oxidized at working electrode 19, a linear relationship exists between the blood glucose concentration and the resulting electrical current.

In sensor 11, substrate 13 provides an insulated structure for mounting the electrodes and membrane layers. Substrate 13 may be between about 0.050 inches and about 0.060 inches wide and between about 1.0 inch and about 2.0 inches long. The thickness of the membrane layers may vary between about 0.5 microns and about 10 microns.

Electrical wires 21 may be coupled or soldered to conductive traces formed on substrate 13 using flex circuit technology. For example, the traces may be gold-plated copper. In one embodiment, sensor 11 may be designed so that the flex circuit terminates to a tab that mates to a multi-pin connector, such as a 3-pin, 1 mm pitch ZIF Molex connector. Such a connection facilitates excitation of working electrode 19 and measurement of electrical current signals, for example, using a potentiostat or other controller.

Electrodes 15, 17 and 19 may be applied to substrate 13 using a thick film process and commercially available inks. In one embodiment, reference electrode 15 may be made using a silver/silver chloride type material deposited or formed on substrate 13. Reference electrode 15 establishes a fixed potential from which the potential of counter electrode 17 and working electrode 19 may be established. The reference potential is Nernstian. For the silver/silver chloride electrode, the reference potential is maintained by the following half-reaction:

$$Ag^0 \rightarrow Ag^+ + e^- \qquad (2)$$

Counter electrode 17 may be constructed from conductive materials such as platinum or graphite. These materials may be formulated as a conductive ink for application to substrate 13 using a thick film process and cured accordingly. Counter electrode 17 provides a working area for conducting the majority of electrons produced from the chemical reaction back to the blood solution or other reactant medium. Without counter electrode 17 in the circuit, the majority of current might pass through reference electrode 15, thereby reducing its service life. Counter electrode 17 may be formed with a surface area greater than that of working electrode 19.

Working electrode 19 may be formed using platinum/graphite materials similar to those used for forming counter electrode 17. In other embodiments, working electrode 19 may be formed from other conductive materials. Its operation has been described thus far as promoting anodic oxidation of hydrogen peroxide at its surface. Other embodiments are possible, for example, working electrode 19 may be held at a negative potential. In this case, the electrical current produced at working electrode 19 may result from reduction of oxygen. In another embodiment, working electrode 19 is held or maintained at a virtual ground and the voltage of counter electrode 17 is adjusted.

In another embodiment shown in FIG. 1B, a sensor 23 may include a second working electrode 25. Sensor 23 may be identical to sensor 11 in all other respects. Second working electrode 25 may be identical in form to first working electrode 19, except for the absence of an enzyme layer. In this case, first working electrode 19 is the active electrode and second working electrode 25 is the inactive electrode. For example, if sensor 23 is configured as a glucose sensor, first working electrode 19 may contain a glucose oxidase layer for reacting with glucose to generate a signal current representing glucose concentration. Second working electrode 25 generates a signal representing all other sources of electric current not resulting from the chemical reaction. A sensing system employing sensor 23 having first and second working electrodes 19 and 25 may then subtract the output of the second working electrode 25 from the output of the first working electrode 19 to obtain a result attributable only to the chemical reaction of interest. Amperometric sensors such as sensors 11 and 23 are typically calibrated at a specific temperature. For sensors intended for intravenous use, the calibration temperature, Tcal, is typically chosen to be normal human body temperature, 98.6° F. or 37° C.

Figure 2:
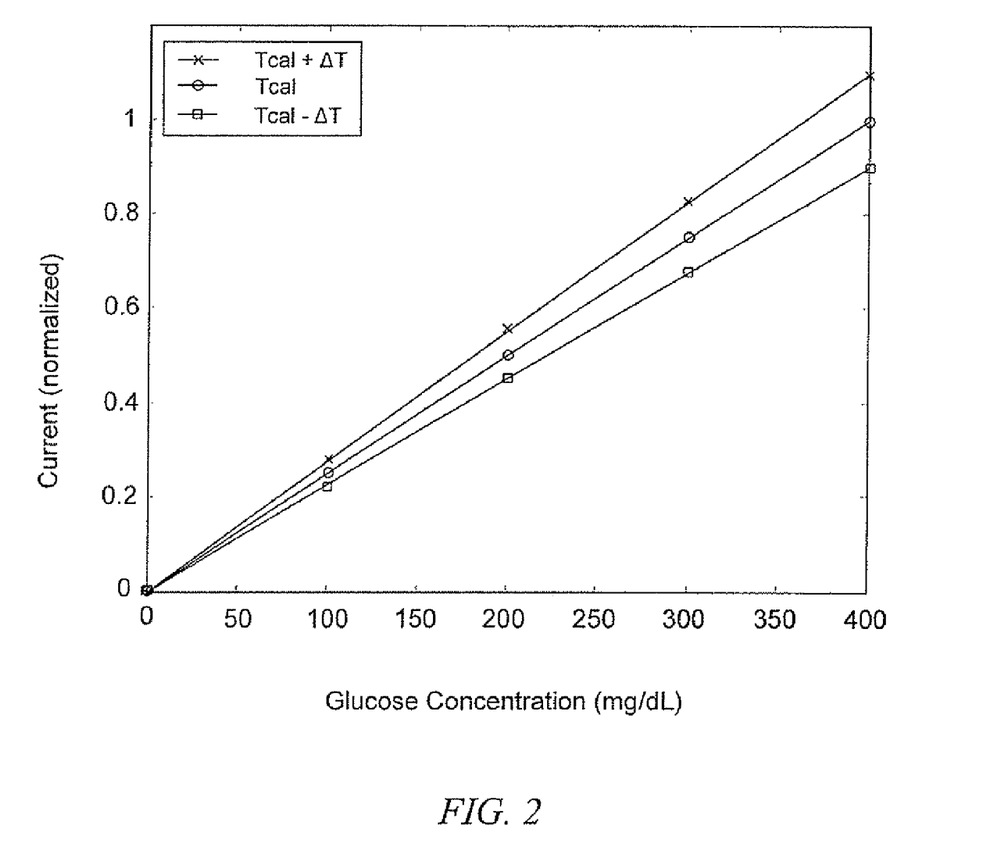
FIG. 2 is a graph illustrating current output from an amperometric glucose sensor as a function of glucose concentration in a blood vessel, and the effect on current output from temperature changes above and below a calibration temperature.

FIG. 2 is a graph illustrating current output from an amperometric glucose sensor as a function of glucose concentration in a blood vessel, and the effect on current output from temperature changes above and below a calibration temperature. As shown in the graph, the measurements obtained from the sensors are somewhat dependent on the temperature of the measurement environment. If the temperature surrounding the sensor changes by +/−ΔT, an error occurs in the measurement. This is because an increase in temperature increases the slope of the curve, and a decrease in temperature decreases the slope of the curve. If the slope increases (i.e. Tcal+ΔT), less glucose is needed to yield a given amount of sensor output and hence, the computed glucose concentration is lower than the actual glucose level. In contrast, if the slope decreases (i.e. Tcal−ΔT), more glucose is needed to yield a given amount of sensor output and so the computed glucose concentration is higher than the actual glucose level. Hence, a change in temperature of the surroundings provides an error in the computed glucose level.

Figure 3:
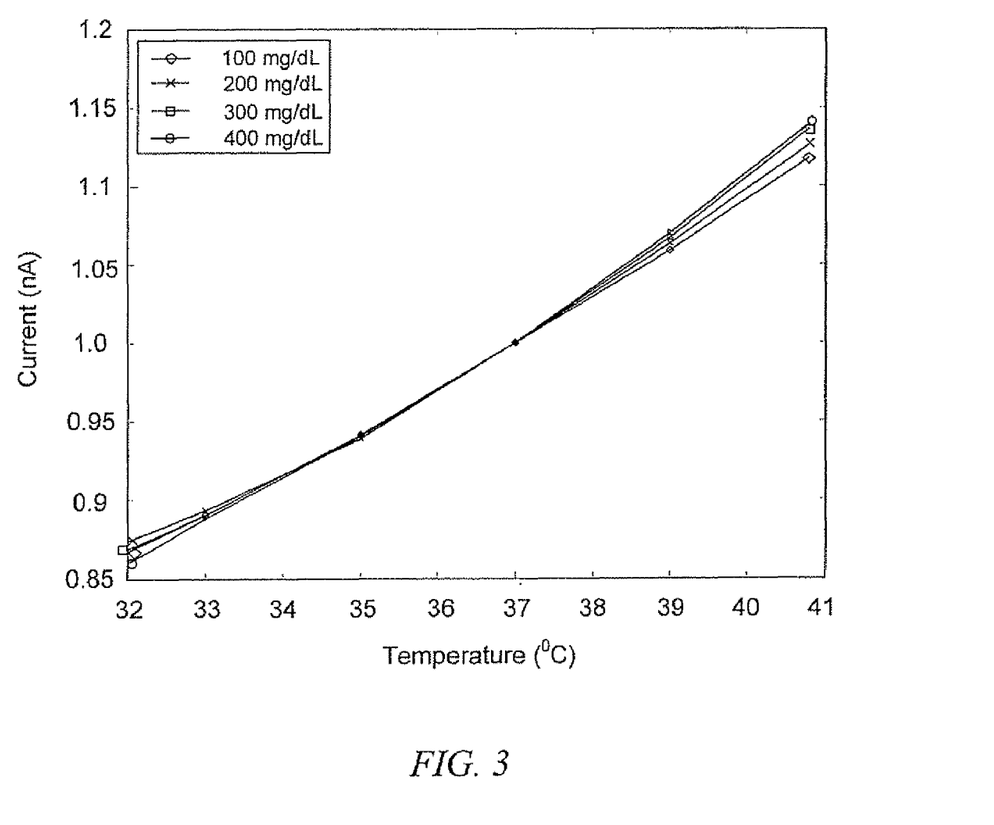
FIG. 3 is a graph illustrating glucose sensor output current as a function of temperature for different values of known glucose concentrations for an amperometric glucose sensor.

FIG. 3 is a graph illustrating glucose sensor output current as a function of temperature for different values of known glucose concentration. Data from a glucose monitoring system was taken at four different glucose concentrations over a temperature range of 32° C. to 41° C. The current was normalized to 1 at 37° C. As shown for the different glucose concentrations, an increase in temperature increases the current measured from the sensor, thereby providing an inaccurate measurement of the glucose level in the blood.

Figure 4:
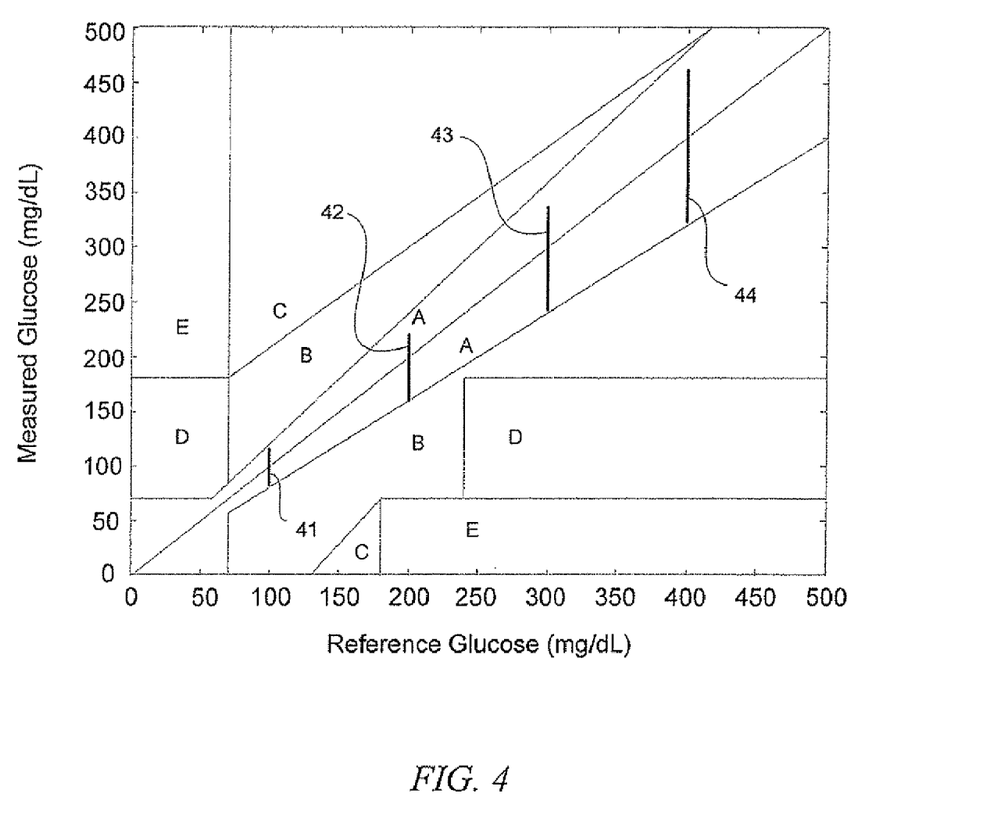
FIG. 4 shows a Clark Error Grid illustrating prior art glucose measurements, without temperature compensation, in relation to known glucose concentration values.

The errors in the data of FIG. 3 are illustrated in the Clark Error grid of FIG. 4. The grid shows how the glucose measurements, without temperature compensation, compare to the true glucose concentration values. FIG. 4 shows five zones: A, B, C, U, and E. Zone A represents clinically accurate measurements. Zone B represents measurements deviating from the reference glucose level by more than 20%, which measurements would likely lead to benign treatment or to no treatment at all. Zone C represents measurements deviating from the reference glucose level by more than 20%, which measurements would likely lead to unnecessary corrective treatment. Zone D represents measurements that are potentially dangerous because they mask abnormal glucose levels and as a result may prevent a physician from detecting and treating blood glucose levels that are outside of a desired range. Zone B represents measurements resulting in erroneous treatment.

The actual test measurements taken using glucose sensors over the temperature range of 32° C. to 41° C. are plotted as vertical lines 41, 42, 43 and 44. As shown in the Clark Error grid, some of the error measurements are on the borderline between Zone A and Zone B. This indicates that a certain percentage of the measurements deviated from the reference by more than 20%. Hence, when no temperature compensation is employed, a particular error generated from this class of sensor may drift into a zone that would lead to unnecessary treatment or prevent a necessary treatment.

Figure 5:
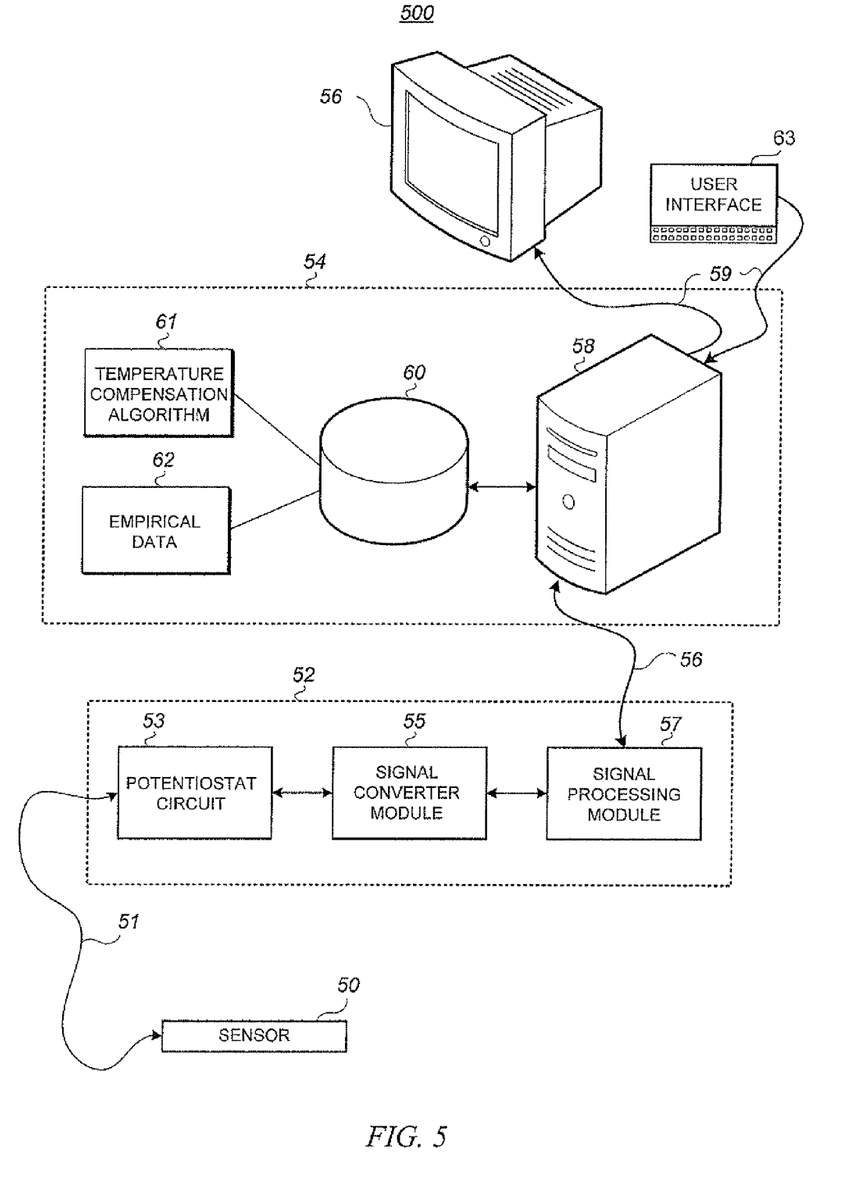
FIG. 5 is a block diagram of a system for monitoring and compensating for temperature measurements in an electrochemical sensor.

FIG. 5 is a block diagram of a system 500 for monitoring and compensating for temperature measurements in an electrochemical sensor. System 500 may be implemented for continuous or intermittent monitoring of a medium of interest, in any of a wide variety of industrial, medical, scientific, and other applications and industries. System 500 may be used as a glucose monitoring system for continuous intravenous measurement of blood glucose concentration in a human patient. System 500 may be implemented in hardware, software and combinations thereof.

System 500 may include a sensor 50, a sensor control unit 52, a computer system 54, and a display unit 56. Sensor 50 may be an amperometric sensor having one or more working electrodes (active or inactive) or may be similar to sensors 11 and 23 previously described. Sensor 50 may be remote from the rest of system 500, and may be coupled to sensor control unit 52 via a cable assembly 51. Cable assembly 51 may include multiple conductors for connecting sensor components to other electronic components within sensor control unit 52. For example, cable assembly 51 may transmit an energization voltage from sensor control unit 52 to sensor 50 and may transmit an electrical current from sensor 50 to sensor control unit 52 that represents a parameter being measured by sensor 50.

Sensor control unit 52 processes measurement signals received from sensor 50 and outputs the processed signals to computer system 54 via communication bus 56. In one embodiment, signals transmitted over communication bus 56 include digital signals. In another embodiment, communication bus 56 may be a USB cable. Sensor control unit 52 may include internal electronic circuits for signal processing. A potentiostat circuit 53 may be included for controlling excitation voltage output to sensor 50, and for receiving measurement signals from sensor 50. A signal converter module 55 may be included for processing analog inputs received from sensor 50. For example, signal converter module 55 may include a lowpass filter, an analog-to-digital converter, and one or more amplifiers. A signal processing module 57 may be included for additional signal processing, for example, to interface with computer system 54. Signal processing module 57 may include a microprocessor or ASIC, digital-to-analog converter, clock, memory, power supply, and other digital electronic components. Signal processing module 57 receives inputs from signal converter module 55 that represents the parameter being measured by sensor 50 and may transmit this signal in digital form (i.e. as a bit stream) via communication bus 56 to computer system 54.

Computer system 54 receives input from sensor 50 via sensor control unit 52, and responsive to the input, may execute one or more algorithms for temperature compensation. Computer system 54 may include a central processor 58, memory 60, and software loaded into memory 60. Central processor 58 may be a microprocessor or a personal computer. Memory 60 is coupled to central processor 58 and may be any computer-readable medium known in the art. In addition to storing operating system software, and other essential software needed for central processor 58 to operate, memory 60 also includes one or more software modules embodying a process for compensating for temperature-related errors in measurements received from sensor 50. These software modules may include a temperature compensation algorithm 61 and an empirical data module 62.

Responsive to sensor input, central processor 58 may execute temperature compensation algorithm 61. When this program is executed, central processor 58 transmits a calibration command to sensor control unit 52 via communication bus 56. The purpose of the calibration command is to cause potentiostat circuit 53 to temporarily reduce the energization voltage applied to sensor 50 to a level below a reaction-sustaining threshold. When the calibration command is issued, signal processing module 57 may convert the command, using a digital-to-analog converter, to an analog signal, which may in turn be filtered and/or amplified by signal converter module 55 for output to potentiostat circuit 53.

The calibration command causes potentiostat circuit 53 to temporarily lower the excitation voltage of sensor 50 to a first voltage level below a reaction-sustaining threshold. For example, on an amperometric glucose sensor bearing glucose oxidase and exposed to blood, the excitation voltage may be temporarily lowered to a level below 450 mV to discourage the oxidation of glucose. This may inhibit the production of hydrogen peroxide, and thus eliminate electrical current flow in sensor 50 that is attributable to the reaction described in Eq. (1). In one embodiment, the first voltage level may be on the order of 100 mV. Other embodiments are possible wherein the first voltage level may be reduced to another value, for example, to a value on the order of 10 mV or 1 mV. As expressed herein, voltage levels are understood to represent absolute values from a reference voltage. The duration of the temporary reduction in the excitation voltage may also vary, and may be on the order of milliseconds, 10 mS, 100 mS, or seconds. The duration may vary according to many factors, including the type of sensor, the response time of the sensor, the medium in which the sensor operates, and the processing speed of the monitoring system.

According to temperature compensation algorithm 61, when sensor excitation voltage is dropped to the first voltage level, central processor 58 may read the resulting sensor output and store this value in memory as an offset current. Central processor 58 may issue a second calibration command to sensor control unit 52. The purpose of the second calibration command is to cause potentiostat circuit 53 to temporarily reduce the energization voltage applied to sensor 50 to a second voltage level below the reaction-sustaining threshold that is different than the first voltage level. When the second calibration command is issued, signal processing module 57 and signal converter module 55 may modify and relay the command as before for output to potentiostat circuit 53. In one embodiment, the second voltage level may be on the order of 50 mV. Other values within the ranges postulated for the first voltage level and its time duration may also be used for the second voltage level. When sensor excitation voltage is adjusted to the second voltage level, central processor 58 may read the resulting sensor output and store this value in memory as another offset current.

When offset current values are obtained for at least two different voltage levels, temperature compensation algorithm 61 may calculate a difference between two offset currents. The offset current difference is indicative of sensor temperature. Temperature compensation algorithm 61 may derive a temperature compensation value based solely or in part on the difference or the slope (e.g., $(i1-i2)/(v1-v2)$). Temperature compensation algorithm 61 may cross-reference the difference to a temperature compensation value maintained in empirical data module 62, for example, by using a lookup table. In another embodiment, temperature compensation algorithm 61 may derive a temperature compensation value using a formula, for example, another algorithm or subroutine provided as part of temperature compensation algorithm 61. The formula that is the basis of the subroutine may also be derived from empirical data 62, which relates a difference in offset currents to a temperature correction value.

Once the temperature compensation value is derived, central processor 58 may issue a command to potentiometer circuit 53 to restore the sensor excitation voltage to its original level that was above the reaction-sustaining threshold. Central processor 58 may receive an uncompensated signal from sensor 50, and according to temperature compensation algorithm 61, add the temperature compensation value to the uncompensated signal to obtain an analyte concentration value (or other sensed parameter) that is now corrected for temperature.

Computer system 54 may output to display unit 56 the temperature-corrected value for the sensed parameter of interest obtained by central processor 58 executing temperature compensation algorithm 61. Display unit 56 may be any visual computer display known in the art. Display unit 56 may be local to computer system 54, or may be remote. In one embodiment, display unit 56 and computer system 54 are an integral component. In another embodiment, display unit 56, computer system 54, and sensor control unit 52 are an integral component. In medical applications, for example, providing a glucose monitoring system in an ICU, ER or OR setting allows display unit 56 to be located within view of an attending physician to provide real-time (or nearly real-time) information on a patient's blood glucose level so that the physician may be immediately apprised of information critical for urgent treatment.

A user interface 63, such as a keyboard, mouse, or touch panel, may be provided as an option. When provided, user interface 63 may wirelessly connect to computer system 54, or directly to central computer 58, to allow for user control over monitoring system operations, appearance of the display, data entry, software installation, system diagnostics, sensor calibrations, network downloading of software, and the like.

Figure 6:
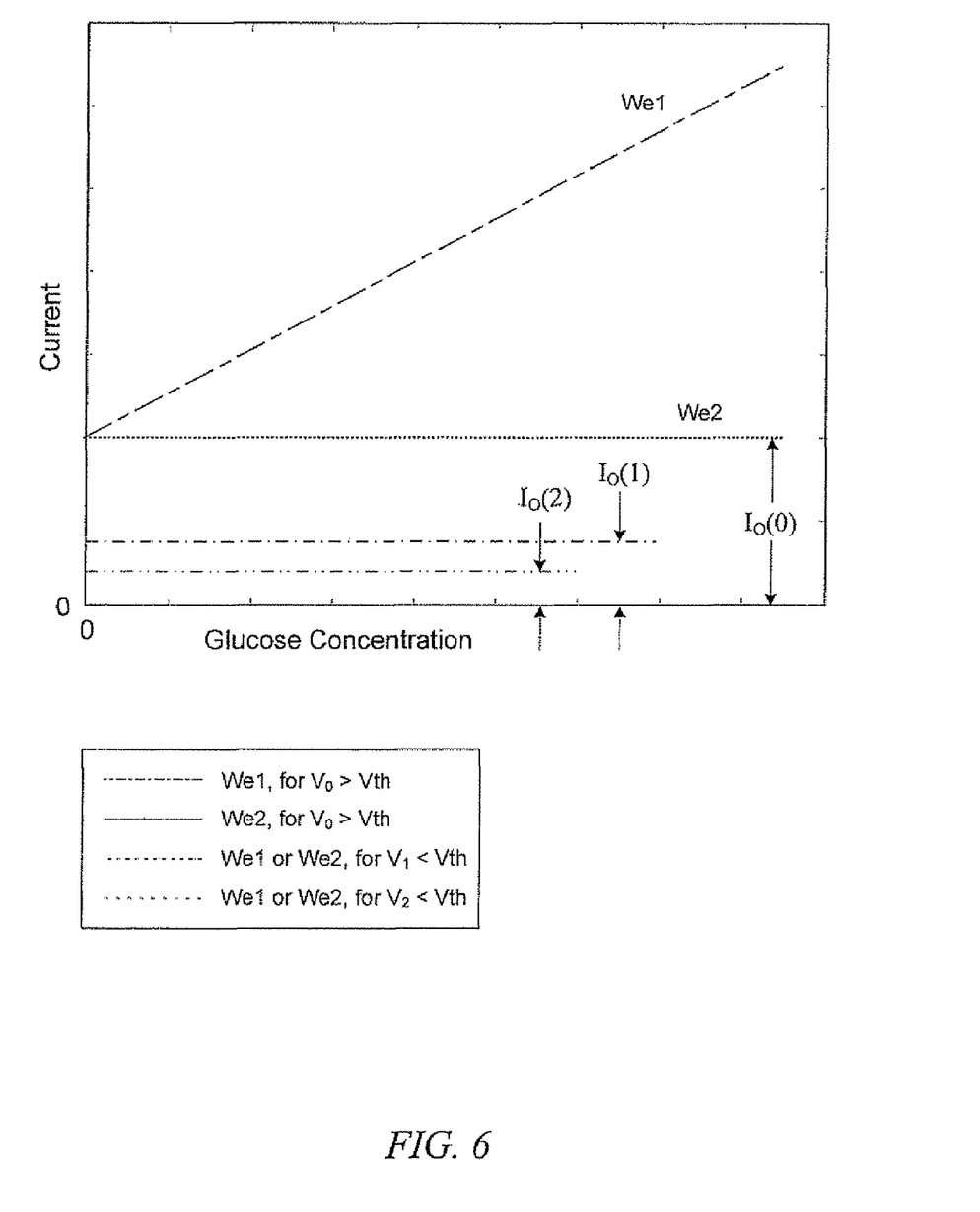
FIG. 6 is a graph of current output vs. glucose concentration for active and non-active working electrodes on a glucose sensor, showing offset current values at different levels of excitation voltage.

FIG. 6 is a graph of current output vs. glucose concentration for active and non-active working electrodes on a glucose sensor, showing offset current values at different levels of excitation voltage. The graph reflects sensor output currents based on an embodiment where there are two working electrodes on the biosensor: a first working electrode We1, which bears a glucose oxidase enzyme, and a second working electrode We2, which is identical to We1 except for the absence of the enzyme. The graph shows offset current values $I_O(0)$, $I_O(1)$, and $I_O(2)$, each corresponding to a different level of excitation voltage applied to one of the working electrodes.

When an excitation voltage greater than a threshold voltage Vth is applied to We1, sensor output as a function of glucose concentration is generally linear, as indicated by the sloped line labeled We1. This output is a combination of a current produced by a chemical reaction, current produced by a sensor configuration, and offset currents that are a function of temperature and a source of error. When an excitation voltage greater than Vth is applied to We2, however, sensor output is generally constant, as indicated by the horizontal line labeled We2. This line represents the offset current $I_O(0)$. By subtracting the offset $I_O(0)$ of sensor electrode We2 from the output of sensor electrode We1, a glucose concentration value may be obtained that is not offset by factors attributable to sensor configuration. However, the resulting signal is still susceptible to temperature-related error.

When excitation voltage applied to either We1 or We2 is lowered to a first voltage level $V_1$ that is below Vth, the sensor may output a first offset current $I_O(1)$, as indicated in the graph. Offset current $I_O(1)$ may be logged in memory by the central computer system. When the excitation voltage applied to either We1 or We2 is lowered to a second voltage level $V_2$ that is below Vth, such that $V_1 \neq V_2$, the sensor may output a second offset current $I_O(2)$, as indicated in the graph. By calculating a difference between offset currents $I_O(1)$ and $I_O(2)$, the central computer system, executing the temperature compensation algorithm 61, may determine a temperature compensation value that corresponds to the calculated difference. The temperature compensation value may then be added (or subtracted or scaled by this value) to the sensor output signal (We1 or We1−We2) to obtain a final result that corrects for temperature-related error. The temperature compensation value may be a scaling factor that is multiplied by the sensor output signal to obtain the final result. The temperature compensation value may be an input to a non-linear scaling function that produces a scaling factor that is multiplied by the sensor output signal. Note that this technique may be applied to a sensor having either one or two working electrodes.

Figure 7:
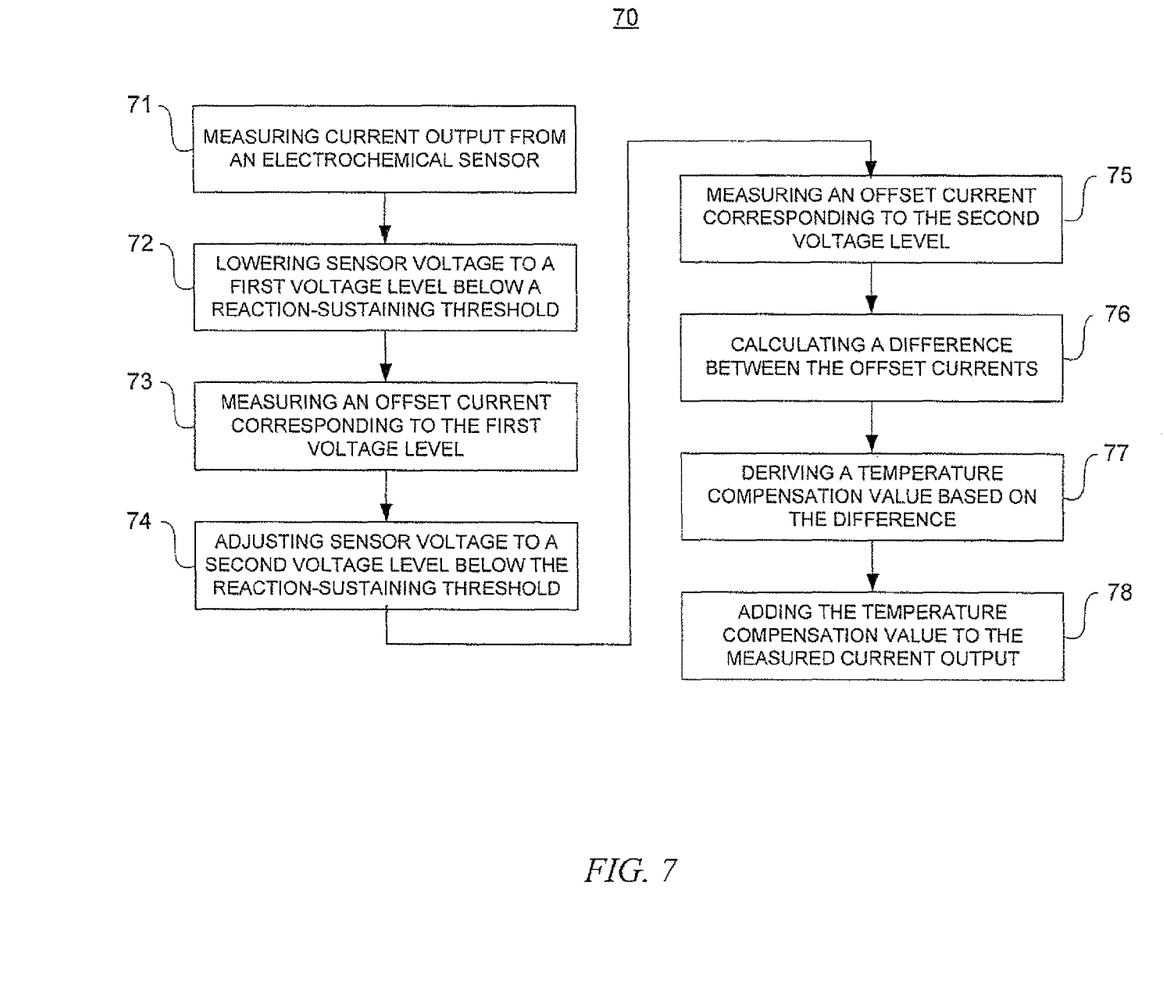
FIG. 7 is a flowchart illustrating process steps for deriving a temperature-corrected value from the output of an electrochemical sensor.

Throughout the foregoing disclosure, various methods according to the invention are described. Method 70, depicted in FIG. 7, is now expressly described as a series of process steps for correcting temperature-related errors in an electrochemical sensor. These process steps may collectively form an algorithm such as a temperature compensation algorithm 61, and are capable of being stored as software in a tangible computer-readable medium and executed by a computer or processor.

Method 70 begins with block 71, in which an output current signal is measured from an electrochemical sensor, e.g., an amperometric glucose sensor. In block 72, excitation voltage of the sensor is lowered to a first voltage level below a reaction-sustaining threshold. In block 73, a measurement is taken of an offset current that corresponds to the first voltage level. Once the value of this offset current is obtained, it may be recorded or stored, prior to executing block 74. In block 74, sensor excitation voltage is adjusted to a second voltage level below the reaction-sustaining threshold, such that the second voltage level is different from the first voltage level. In block 75, an offset current corresponding to the second voltage level is obtained, and may be recorded or stored.

The next two blocks may be implemented by a computer system or processor coupled to the sensor. In block 76, a value is obtained as the difference between the offset current corresponding to the first voltage level and the offset current corresponding to the second voltage level. Once the difference is obtained, block 77 may be performed. In block 77, a temperature compensation value is derived based solely or in part on the difference obtained in block 76. In one embodiment, the temperature compensation value may be obtained using a lookup table. In another embodiment, the temperature compensation value may be obtained by running an algorithm or subroutine that computes the compensation value as a function of the offset currents according to a formula. In block 78, the temperature compensation value is added to the measurement taken in the previous step to obtain a final value from the sensor that is corrected for temperature.

The principles of the invention are to be interpreted broadly, and are not limited to glucose sensors, enzyme electrodes, or to amperometric sensors in general. Those skilled in the art will readily grasp that the invention may be applied to other electrodes, sensors, and instrumentation systems that are affected by temperature fluctuation. Accordingly, the terminology employed throughout the disclosure should be read in an exemplary rather than a limiting manner. Although minor modifications of the invention will occur to those well versed in the art, it shall be understood that what is intended to be circumscribed within the scope of the patent warranted hereon are all such embodiments that reasonably fall within the scope of the advancement to the art hereby contributed, and that that scope shall not be restricted, except in light of the appended claims and their equivalents.

The invention claimed is:

1. A method of compensating for temperature-related errors in an electrochemical sensor that outputs a current proportional to an analyte concentration when a voltage is applied to the sensor, the method comprising:
   measuring current output from the sensor;
   lowering sensor voltage to a first voltage level below a reaction-sustaining threshold;
   measuring a first offset current corresponding to the first voltage level;
   adjusting sensor voltage to a second voltage level below the reaction-sustaining threshold, wherein said second voltage level is different from said first voltage level;
   measuring a second offset current corresponding to the second voltage level;
   calculating a difference between the first and second offset currents;
   deriving a temperature compensation value based in part on the difference; and
   adding the temperature compensation value to the measured current output to obtain an analyte concentration corrected for temperature.

2. The method of claim 1 wherein the sensor voltage is applied to a counter electrode or a working electrode on the electrochemical sensor.

3. The method of claim 1 wherein the sensor comprises a glucose sensor.

4. The method of claim 3 wherein the glucose sensor includes glucose oxidase.

5. The method of claim 1 wherein the sensor comprises first and second working electrodes.

6. The method of claim 5 wherein the first working electrode comprises glucose oxidase and the second working electrode comprises a reference electrode.

7. The method of claim 1 wherein the reaction-sustaining threshold is a reduction threshold or an oxidation threshold.

8. The method of claim 1 further comprising displaying a value representing the temperature-corrected analyte concentration.

9. A system for compensating for temperature-related errors in an electrochemical sensor that outputs a current proportional to an analyte concentration when a voltage is applied to the sensor, comprising:
   a sensor having a working electrode;
   a potentiostat for adjusting voltage applied to the working electrode;
   a processor coupled to memory; and
   temperature compensation software stored in the memory and executable by the processor, wherein responsive to the processor executing the software, the potentiostat temporarily lowers the voltage of the working electrode to a first voltage level below a reaction-sustaining threshold, and thereafter to a second voltage level below that reaction-sustaining level, and wherein said first and second offset currents measured at said first and second voltage levels are then compared to obtain a temperature compensation value for correcting sensor output when the voltage of the working electrode is raised above the reaction-sustaining threshold, wherein said first and second voltage levels are different from one another.

10. The system of claim 9 wherein the sensor comprises a glucose sensor.

11. The system of claim 10 wherein the glucose sensor includes glucose oxidase.

12. The system of claim 9 further comprising a display coupled to the processor for displaying analyte concentration corrected according to the temperature compensation value.

13. The system of claim 9 wherein the reaction-sustaining threshold is a reduction threshold or an oxidation threshold.

* * * * *

UNITED STATES PATENT AND TRADEMARK OFFICE
CERTIFICATE OF CORRECTION

PATENT NO. : 8,000,918 B2  
APPLICATION NO. : 12/205634  
DATED : August 16, 2011  
INVENTOR(S) : Fjield et al.

It is certified that error appears in the above-identified patent and that said Letters Patent is hereby corrected as shown below:

In the Specification

Column 6,  
Line 47, "zones: A, B, C, U, and E" should be --zones: A, B, C, D, and E--.  
Line 58, "Zone B represents" should be --Zone E represents--.

Signed and Sealed this  
Twenty-ninth Day of March, 2016

Michelle K. Lee  
*Director of the United States Patent and Trademark Office*